(12) United States Patent
Fergason

(10) Patent No.: US 7,150,047 B2
(45) Date of Patent: Dec. 19, 2006

(54) INDICATOR LAYOUT ON AN AUTO-DARKENING LENS FOR USE IN WELDING

(75) Inventor: John D. Fergason, Cupertino, CA (US)

(73) Assignee: LightSwitch Safety Systems, Inc., Mountain View, CA (US)

(*) Notice: Subject to any disclaimer, the term of this patent is extended or adjusted under 35 U.S.C. 154(b) by 141 days.

(21) Appl. No.: 10/884,047

(22) Filed: Jul. 2, 2004

(65) Prior Publication Data

US 2005/0002083 A1   Jan. 6, 2005

Related U.S. Application Data

(60) Provisional application No. 60/484,910, filed on Jul. 2, 2003.

(51) Int. Cl.
*A61F 9/06* (2006.01)

(52) U.S. Cl. .................... 2/8.1; 2/427; 340/815.45

(58) Field of Classification Search .............. 2/8, 2/906, 5, 7, 432, 427, 426; 340/815.45
See application file for complete search history.

(56) References Cited

U.S. PATENT DOCUMENTS

| | | | | |
|---|---|---|---|---|
| 2,045,801 | A | * | 6/1936 | Richter .................. 315/133 |
| 2,045,802 | A | * | 6/1936 | Richter .................. 340/815.73 |
| 3,731,986 | A | | 5/1973 | Fergason |
| 3,881,809 | A | | 5/1975 | Fergason et al. |
| 4,039,254 | A | | 8/1977 | Harsch |
| 4,078,856 | A | * | 3/1978 | Thompson et al. ......... 359/296 |
| RE29,684 | E | | 6/1978 | Gordon |
| 4,283,798 | A | * | 8/1981 | Kuehn ..................... 2/426 |
| 4,385,806 | A | | 5/1983 | Fergason |
| 4,436,376 | A | | 3/1984 | Fergason |
| 4,462,661 | A | * | 7/1984 | Witt ....................... 349/14 |
| 4,540,243 | A | | 9/1985 | Fergason |
| 4,582,396 | A | | 4/1986 | Bos et al. |
| RE32,521 | E | | 10/1987 | Fergason |
| 4,719,462 | A | * | 1/1988 | Hawkins .................. 342/20 |
| 5,074,647 | A | | 12/1991 | Fergason et al. |
| 5,078,130 | A | * | 1/1992 | Van Oosten et al. ..... 128/201.24 |
| 5,191,317 | A | * | 3/1993 | Toth et al. .............. 340/626 |
| 5,200,736 | A | * | 4/1993 | Coombs et al. ........... 340/586 |
| 5,208,688 | A | | 5/1993 | Fergason et al. |
| 5,248,880 | A | | 9/1993 | Fergason |
| 5,252,817 | A | | 10/1993 | Fergason et al. |
| 5,347,383 | A | | 9/1994 | Fergason |

(Continued)

FOREIGN PATENT DOCUMENTS

CA   2076777   2/1993

(Continued)

OTHER PUBLICATIONS

International Search Report relating to application PCT/US2004/021401, dated mailed Dec. 8, 2004.

*Primary Examiner*—Rodney M. Lindsey
(74) *Attorney, Agent, or Firm*—Renner, Otto, Boisselle & Sklar, LLP

(57) ABSTRACT

An indicator system and method for an auto-darkening lens or other device that is intended to be placed relatively close to the face of a wearer includes one or more indicators adjacent the lens and generally provides the indicators in the peripheral field of view of the wearer, allowing the indicators to be discerned without having to focus eye vision on them and while allowing the wearer to direct eye focus on a work piece or the like.

45 Claims, 4 Drawing Sheets

U.S. PATENT DOCUMENTS

| | | | |
|---|---|---|---|
| 5,420,828 A * | 5/1995 | Geiger ........................ 367/131 |
| 5,481,440 A * | 1/1996 | Oldham et al. ............. 362/555 |
| 5,510,609 A | 4/1996 | Ackermann |
| 5,519,122 A | 5/1996 | Ajito et al. |
| 5,519,522 A | 5/1996 | Fergason |
| 5,671,035 A | 9/1997 | Barnes |
| 5,751,258 A * | 5/1998 | Fergason et al. ................ 345/7 |
| 5,764,203 A * | 6/1998 | Holmlund et al. .............. 345/8 |
| 5,813,990 A * | 9/1998 | Ryll .......................... 600/500 |
| 5,959,705 A | 9/1999 | Fergason |
| 6,067,129 A | 5/2000 | Fergason |
| 6,070,264 A | 6/2000 | Hamilton |
| 6,075,445 A * | 6/2000 | McLoughlin et al. ....... 340/586 |
| 6,242,711 B1 | 6/2001 | Cooper |
| 6,246,505 B1 * | 6/2001 | Teowee et al. .............. 359/241 |
| 6,270,223 B1 * | 8/2001 | Del Bon et al. ............. 359/601 |
| 6,298,498 B1 * | 10/2001 | Burns et al. .................... 2/424 |
| 6,369,952 B1 | 4/2002 | Rallison et al. |
| 6,700,497 B1 * | 3/2004 | Hibbs et al. ................. 340/584 |
| 6,734,393 B1 * | 5/2004 | Friedl et al. ................. 219/132 |
| 2005/0002083 A1* | 1/2005 | Fergason .................... 359/276 |
| 2005/0017152 A1* | 1/2005 | Fergason .................... 250/205 |

FOREIGN PATENT DOCUMENTS

DE    41 28 291 A1    3/1993
EP    65578 A1 *    12/1982
EP    1 118 899 A1    7/2001

\* cited by examiner

INDICATOR LAYOUT ON AN AUTO-DARKENING LENS FOR USE IN WELDING

CROSS-REFERENCE TO RELATED APPLICATION

This application claims the benefit of U.S. Provisional Application Ser. No. 60/484,910, filed Jul. 2, 2003.

TECHNICAL FIELD

The present invention relates generally, as indicated, to an indicator layout for an auto-darkening lens and devices using an auto-darkening lens, and more specifically to an indicator system and method to convey information to a person wearing a shield device or the like over at least part of the face that includes an auto-darkening lens.

BACKGROUND

As is described further in the background discussion below, it is difficult to provide information indicating operative condition, status, and the like of a variable shutter or lens that is used to protect the eyes of a person if that lens or shutter is located in close proximity to the eyes. Because of the close proximity of the lens or shutter, it is difficult, if not impossible, accurately or conveniently to focus the eyes on status indicators or the like that are proximate the shutter or lens. Examples of such a shutter or lens include an auto-darkening welding lens used in a welding helmet, a similar auto-darkening lens used in a respirator system that employs a helmet or other face covering, etc. Exemplary information that may be conveyed to the person wearing the helmet, respirator, etc., may be shade number, sensitivity, power level, power or battery reserve, etc.

In the description herein reference will be made to a lens (also sometimes referred to as "welding lens," "welding filter," "shutter," and the like), and to an automatically darkening lens (sometimes referred to as auto-darkening lens) that is able to operate automatically to control the transmission of light through the lens. The lens may be a light shutter type of a device that is able to control light transmission without distorting, or at least with relatively minimal distortion of, the light and the image characteristics carried by the light or represented by the light. Therefore, when a person looks through the lens, the image seen would be substantially the same as the image seen without the lens, except that the intensity of the light transmitted through the lens may be altered depending on the operative state of the lens. The lens may be used in a welding helmet, and the lens may be used in other types of devices, such as goggles, spectacles, face masks, e.g., for industry (such as in an industrial plant or to protect outdoor or indoor electrical workers), for dentistry to protect the fact of a dentist in the operative, respirator systems, nuclear flash eye protection devices, and other types of helmets and other eye-protection devices, etc. Such devices usually are employed to protect the face or the eyes of a person, as is known, for example, in the field of welding as well as other fields. Further, the lenses may be used in various other places to protect workers from bright light that could present a risk of injury.

For the purposes of providing eye protection, usually a welding lens provides light blocking characteristics in the visible, infrared and ultraviolet wavelength ranges. The actual ranges may be determined by the components of the lens, the arrangement of those components, and so forth.

One example of such a welding lens is described in U.S. Pat. No. 5,519,522. The lens assembly disclosed in that patent includes several liquid crystal cell light shutters, several plane polarizers, and a reflector or band pass filter, that are able to reflect ultraviolet and infrared electromagnetic energy and possibly also some electromagnetic energy in the visible wavelength range. The several liquid crystal cells, for example, may be birefringent liquid crystal cells sometimes referred to as surface mode liquid crystal cells or pi-cells.

As will be described further below, the present invention may be embodied in a variable optical transmission controlling device. Such a device is described in detail with respect to use in a welding helmet. However, it will be appreciated that such a device may be employed in other environments and in other devices and systems for controlling transmission of electromagnetic energy broadly, and, in particular, for controlling optical transmission. As used herein with respect to one example, optical transmission means transmission of light, i.e., electromagnetic energy that is in the visible spectrum and that also may include ultraviolet and infrared ranges. The features, concepts, and principles of the invention also may be used in connection with electromagnetic energy in other spectral ranges.

Examples of liquid crystal cells, lenses using them and drive circuits are described in U.S. Pat. Nos. 5,208,688, 5,252,817, 5,248,880, 5,347,383, and 5,074,647. In U.S. Pat. No. 5,074,647, several different types of variable polarizer liquid crystal devices are disclosed. Twisted nematic liquid crystal cells used in an automatic shutter for welding helmets are disclosed in U.S. Pat. Nos. 4,039,254 and Re. 29,684. Exemplary birefringent liquid crystal cells useful as light shutters in the present invention are disclosed in U.S. Pat. Nos. 4,385,806, 4,436,376, 4,540,243, 4,582,396, and Re. 32,521 and exemplary twisted nematic liquid crystal cells and displays are disclosed in U.S. Pat. Nos. 3,731,986 and 3,881,809.

Another type of liquid crystal light control device is known as a dyed liquid crystal cell. Such a dyed cell usually includes nematic liquid crystal material and a pleochroic dye that absorbs or transmits light according to orientation of the dye molecules. As the dye molecules tend to assume an alignment relative to the alignment of the liquid crystal structure or directors, a solution of liquid crystal material and dye placed between a pair of plates will absorb or transmit light depending on the alignment of the liquid crystal material. Thus, the absorptive characteristics of the liquid crystal device can be controlled as a function of applied electric field.

As is disclosed in several of the above patents, the respective shutters may have one or more operational characteristics (sometimes referred to as modes or states). One example of such an operational characteristic is the shade number; this is the darkness level or value of the shutter when it is in the light blocking mode. Another exemplary operational characteristic is the delay time during which the shutter remains in a dark state after a condition calling for the dark state, such as detection of the bright light occurring during welding, has ceased or detection thereof has terminated or been interrupted. Still another operational characteristic is sensitivity of one or both of the detection circuit or shutter to incident light, for example, to distinguish between ambient conditions and the bright light condition occurring during a welding operation and sensitivity also may refer to shutter response time or to the time required for the circuitry associated with the lens to detect a sharp increase in incident light (e.g., due to striking of the welding arc, etc.) and to switch the lens from the clear state to the dark state. Yet another characteristic, which may be considered an operational characteristic, is the condition of the battery or other power source for the shutter, such as the amount of power remaining, operational time remaining until the power source becomes ineffective, etc. In the past various operational characteristics of such shutters have been adjustable or fixed.

Dynamic operational range or dynamic optical range is the operational range of the lens between the dark state and the clear state, e.g., the difference between the shade numbers of the dark state and the clear state.

An example of a "welding lens with integrated display and method" is disclosed in U.S. Pat. No. 6,067,129. As disclosed therein the current operational characteristics of a shutter can be displayed and can be selectively changed by operating one or more switches. The switches may be flexible membrane switches, microswitches, or another type of switch.

The disclosures of the patents identified herein are specifically incorporated in their entirety by reference.

SUMMARY

The present invention is useful for eye protection by an automatically darkening light shutter in a helmet or goggle assembly or in another device, if desired. The switching mechanism for powering the light shutter on and off or for selecting operational characteristics may be an integral part of the light shutter or frame assembly or other component or portion thereof.

The light shutter of the present invention may be used in a variety of embodiments and applications. The shutter is adjustable to control light, i.e., to increase or to decrease the amount of the incident light which is transmitted through the shutter. When welding is not occurring, for example, the shutter in a welding helmet may be substantially optically clear or transmissive or at least minimizes its attenuation of light. When welding is occurring, the shutter may be dark or closed to reduce the amount of light transmitted therethrough in order to protect the eyes of the person performing the welding and maximize his or her viewing comfort. In both cases, though, the image characteristics of the light preferably remain intact. A photosensitive device may be used to sense the intensity of light impinging in the area of the shutter so as to provide an input to a drive circuit for the shutter in order to control opening and closing thereof.

According to an aspect of the invention, an indicator system for a head mountable apparatus includes a number of indicators, an input to provide selective inputs to the indicators to cause the indicators to provide output indications, the indicators being in the peripheral field of view of a wearer of such head mountable apparatus in ordinary use, the indicators being located relative to each other, whereby the indications provided thereby may be comprehended based on at least one of relative location to each other and location in such head mountable apparatus.

Another aspect relates to a protective apparatus for at least a portion of the face of a wearer, including a protective shield positionable with respect to the face of a wearer, a viewing area to permit viewing through the shield, and a number of indicators to indicate information to a wearer, the indicators being located at least one of relative to each other and to the shield to provide information to a wearer based on energization and location of such indicators.

Another aspect relates to a protective apparatus for at least a portion of the face of a wearer, including a protective shield positionable with respect to the face of a wearer, a viewing area to permit viewing through the shield, and an indicator for indicating information to a wearer by providing information to a wearer based on energization and location of such indicator relative to the field of view of a wearer.

Another aspect relates to a method of conveying information to a person wearing a shield device protecting at least part of the wearer's face, including selectively energizing one or more respective indicators positioned with respect to the shield to convey information to the person based on the relative position of the respective energized one or more indicators.

These and other objects, features, advantages and functions of the invention will become more apparent as the following description proceeds.

It will be appreciated that although the invention is described with respect to one or more embodiments, the scope of the invention is limited only by the claims and equivalents thereof. It also will be appreciated that if the invention is described with respect to several embodiments, features of a given embodiment also may be used with one or more other embodiments.

Also, although the invention is described with respect to a welding shutter (also known as a light shutter) used in a welding helmet for eye protection therein, it will be appreciated that the various features of the invention may be used in conjunction with other devices and functions.

To the accomplishment of the foregoing and related ends, the invention, then, includes the features hereinafter described in the specification and particularly pointed out in the claims, the following description and the annexed drawings setting forth in detail certain illustrative embodiments of the invention, these being indicative, however, of but several of the various ways in which the principles of the invention may be suitably employed.

BRIEF DESCRIPTION OF THE DRAWINGS

In the annexed drawings:

FIG. 7 is a schematic side elevation view of an auto-darkening lens in a respirator, space helmet or the like;

DESCRIPTION

Figure 1:
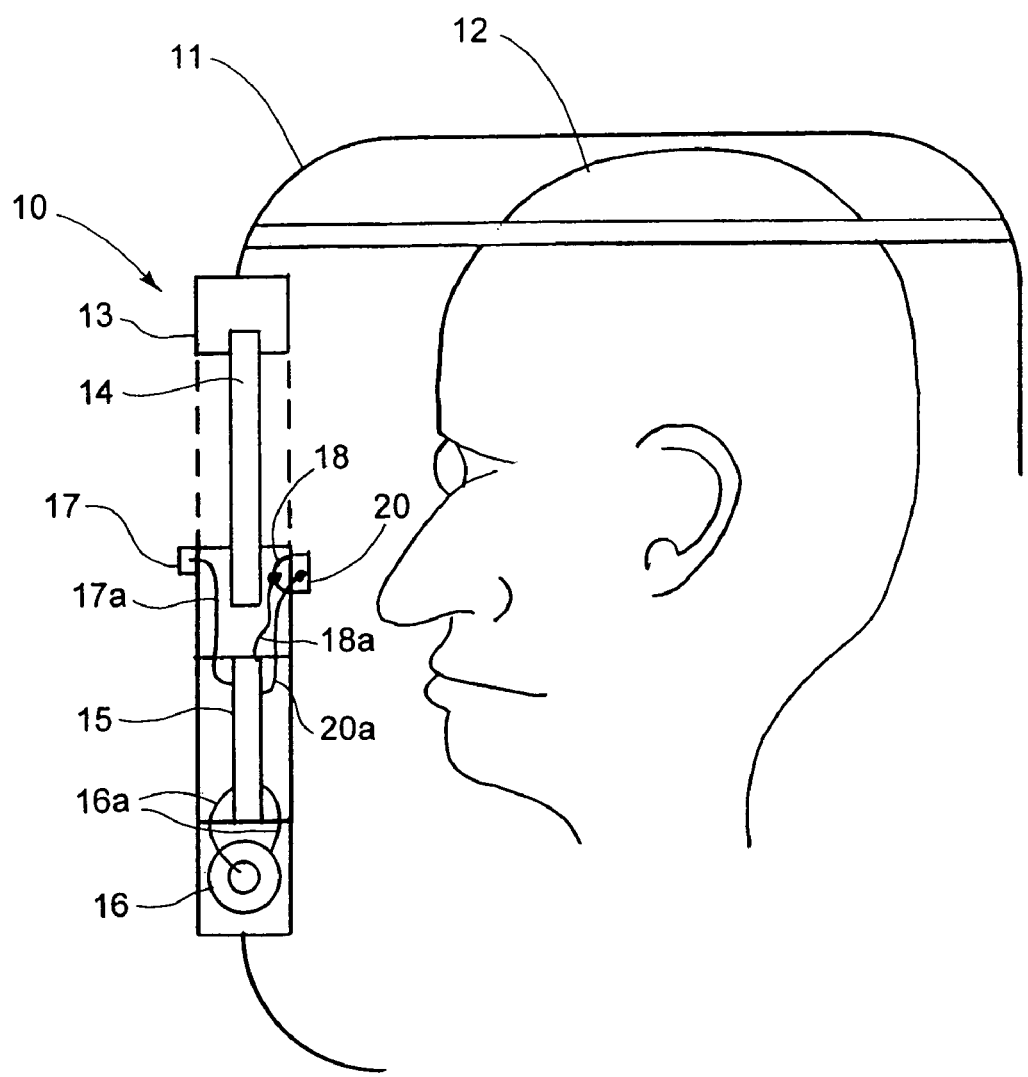
FIG. 1 is a schematic side elevation view, broken away, of an auto-darkening lens in a welding helmet in place on the head of a wearer.
Figure 2:
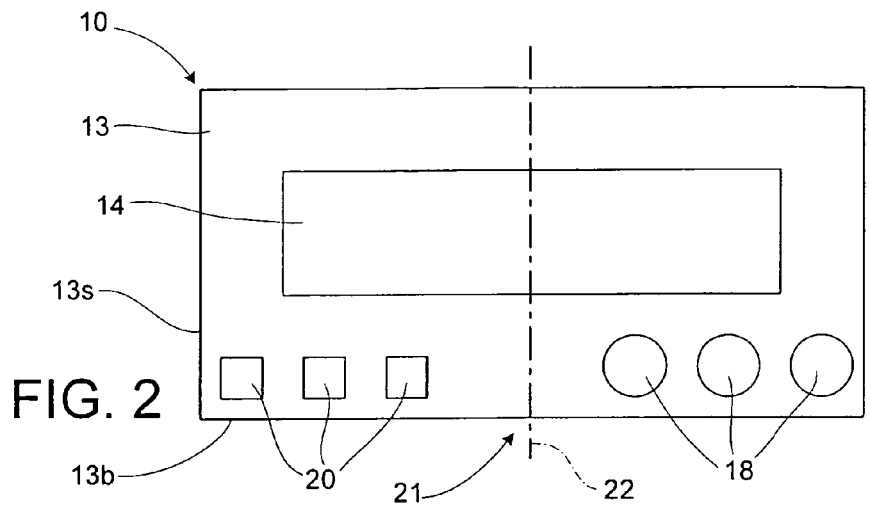
FIG. 2 is a back plan view of the auto-darkening lens of FIG. 1 illustrating horizontally oriented/spaced-apart indicators.

Referring now to the drawings, and initially to FIGS. 1 and 2, an auto-darkening lens 10 is illustrated in a welding helmet 11 in position on the head of a wearer 12 (sometimes referred to as a user). In the description below primed reference numerals are used to represent parts that are similar to parts that are designated by the same unprimed reference numeral. Reference to directions, such as horizontal, vertical, left, right, up, down, is for relative reference in the illustrated embodiments only and is not intended to be limiting.

The auto-darkening lens 10 includes, for example, a support structure or housing 13, a variable light transmission shutter 14 mounted with respect to the support structure, operating circuitry 15 and a power supply 16. The shutter 14 may be of the type disclosed in the above patents or some other suitable shtter that provides controllable variable light transmission capability and operation. Connections 16a couple the power supply 16 to provide power to the operating circuitry 15. Associated with the operating circuitry 15 is a photosensor 17, which is coupled to the operating circuitry by connections 17a, to sense occurrence of or a condition requiring a need for the auto-darkening lens 10 to darken or to lighten, e.g., to decrease light transmission during welding or to increase light transmission in the absence of welding. The operating circuitry 15 operates the auto-darkening lens to various conditions of light transmission. Several control buttons and switches schematically shown at 18 in FIGS. 1 and 2 are coupled by connections 18a to the operating circuitry 15 and may be operated by the wearer 12 to turn on the operating circuitry 15 to operate the shutter 14, e.g., to adjust the desired degree of shade, to set a delay time, to set sensitivity, etc. As an example, the switches 18 may be membrane switches. One or more of the switches 18 may be a variable resistor or other adjustable electrical or electronic component; several non-limiting examples include a potentiometer, a stepped resistance, resistor or capacitor, respective capacitors, etc. The operating circuitry 15, power supply 16, photosensor 17, and buttons and switches 18 may be mounted on, in or part on and part in the support structure or may be otherwise located, as may be desired.

In use of the auto-darkening lens 10 in the welding helmet 11, a wearer 12 may turn on the power and set the desired dark shade of the shutter 14 by using the buttons and switches 18. The wearer then puts the welding helmet 11 on the head with the shutter in front of the eyes for viewing work. The shutter 14 may be in its relatively clear or high light transmission condition (or state) to allow the wearer to view the work; and upon sensing occurrence of welding, the photosensor 17 indicates the same to the operating circuitry to cause the shutter to assume a dark or relatively reduced light transmission condition (or state). When welding ceases, the operating circuitry allows the shutter to return to the relatively clear condition.

Indicators 20 indicate operating conditions of the auto-darkening lens 10. The indicators 20 may be coupled, as at 20a, to the operating circuitry or to some other device that operates the indicators. Examples of operating conditions may include, without limitation, the current shade or light transmitting condition of the shutter 14, e.g., is it clear or dark; reserve power supply power level, e.g., how much charge remains in the power supply (such as a battery) before becoming unable to supply adequate power to the operating circuitry 15 to operate the shutter 14; whether power from an external source is connected for operating the auto-darkening lens; whether the auto-darkening lens 10 is on, e.g., is receiving power to the operating circuitry 15; what shade level has been set, e.g., by the buttons and switches 18; what delay time and/or sensitivity has been set, e.g., by the buttons and switches 18; etc.

The indicators 20 may be of the type that provide a light output. For example, each indicator may be a light emitting diode, an organic light emitting diode, an incandescent bulb, a combination of a light source and a light modulating device, such as a liquid crystal light modulator, or other type of device that provides a light output or indication based on light in response to an appropriate energization. The light output may be the generating or emitting of light by a given light source or it may be modulation of the light from a light source. The light output may be white, may be of a given color, or may be of different respective colors.

Operation of the indicators 20 may be provided by the operating circuitry 15. For example, the operating circuitry may provide respective signals and, if needed, power to cause respective indicators to provide a light output, to modulate light from a light source, to provide respective colors of light, etc. Such respective signals from the operating circuitry 15 may indicate the above-mentioned operating conditions of the auto-darkening lens 10 or other information that may be of interest, useful or needed by the wearer 12.

Location of the indicators 20 is such that they would generally be in the peripheral field of view of the wearer 12 when the wearer is wearing the auto-darkening lens in a usual operative position with respect to the eyes of the wearer 12 and the wearer is looking through the shutter 14. The indicators 20 may be mounted on the support structure or housing 13 or may be mounted elsewhere, provided in use with the auto-darkening lens 10 in place before the eyes of the wearer 12, the indicators generally are in the peripheral field of view of the wearer. With the auto-darkening lens 10 before the eyes of the wearer, the indicators 20 would be so close to the face of the wearer that it would be difficult, if not impossible, for the wearer to focus an eye on the indicators as to see them clearly with good focus.

As is illustrated in FIGS. 1 and 2, the indicators 20 are at the bottom of the auto-darkening lens 10 and are mounted on the support structure 13; and the indicators are arranged in a row to the left side 21 of approximate center, e.g., vertical centerline 22, of the auto-darkening lens. Other orientations are possible, examples of which are described below.

In the illustrated embodiment of FIGS. 1 and 2 the indicators 20 are located to only one side of the centerline 22. Locating the indicators only on one side of the centerline 22 helps to avoid confusion as to which of the indicator (or indicators) is illuminated. Since the nose of the wearer tends to separate at least part of the peripheral views of the respective eyes of the wearer, locating the indicators 20 on only one side of the centerline 22, which ordinarily lines up approximately with the nose of the wearer, tends to have such indicators seen only by one eye of the wearer. By locating the indicators 20 as described, then even without directly viewing them in focus by an eye of the wearer the relative positions of respective indicators usually can be discerned. Also, the angle at which the indicator(s) 20 is seen by the wearer can help the wearer to discern which indicator(s) is energized and, thus, convey information to the wearer. Therefore, information can be conveyed to the wearer by the indicators 20 based on the relative location of the energized (or not energized) indicator(s) in the peripheral field of view, based on the relative location of an indicator to other indicators, and based on the angle at which the indicator(s) is seen in the peripheral field of view.

The spacing of the indicators 20 relative to each other may be such that it is relatively easy for a user to distinguish the relative positions thereof. This arrangement facilitates using the positional relation of energized and/or unenergized indicators to convey information to the user.

Having the indicators on both sides of the centerline 22 may tend to cause confusion as to information being conveyed. However, the indicators may be at both sides of the viewing window, e.g., the sides of the shutter 14, and in such case ordinarily the indicator(s) at only one side at a time would be active to provide a light output, for example, so as to avoid possible apparent superimposition problems and confusion to the wearer.

However, if indicators were located at both sides of the centerline, it would be desirable to provide some characteristic to facilitate distinguishing which indicator is being discerned. For example, the indicators on one side could be arranged in a horizontal pattern and those on the other side in a vertical pattern. Color also may be used for distinguishing between indicators on respective sides of the centerline.

It is possible to provide distinguishing features to one or more of the indicators, such as color, intensity, flashing/not flashing, etc.

Depending on the proximity of the indicators 20 to the face of the wearer 12, the indicators may be closer or further from the eyes of the wearer. For example, the indicators may be relatively close to the ordinary field of view if they are located relatively close to the face of the wearer; and they may be relatively further from the ordinary field of view if they are located relatively far from the ordinary field of view of the wearer. Therefore, if the indicators 20 are mounted on the support structure 13 and the auto-darkening lens 10 usually is worn close to the face and eyes of the wearer 12, the indicators 20 may be relatively close to the shutter 14; but if the auto-darkening lens usually is worn relatively further from the face and eyes of the wearer, the indicators could be positioned relatively further away from the shutter.

Energization of the indicators 20 may be effected by inputs from the operating circuitry 15, as was mentioned above. For example, the operating circuitry may include a monitor to detect the amount of power (power reserve) remaining in a battery power supply for the auto-darkening lens; and in response to that detection the operating circuitry may illuminate a given indicator 20 or several indicators to indicate there is adequate power, the amount of power, e.g., the amount of time left before power runs out, that power will run out shortly, etc. If the power were to run out shortly, it would be desirable for the wearer to plan to stop working, e.g., welding, shortly and in any event before the power runs out, thereby to avoid the possibility that the work would be continued while the eyes would be unprotected by the dark state of the shutter 14. The operating circuitry 15 may provide an input to one or several indicators to indicate the pre-set shade level to which the shutter 14 will be operated when it is in the dark state, or to indicate response speed of the shutter, sensitivity level of the shutter, e.g., sensitivity of the photosensor 17 and operating circuitry to cause the shutter to be operated in the dark condition. The operating circuitry 15 may provide an input to one or several indicators to indicate that the shutter 14 is in a clear state condition or a dark state condition; this is valuable information because sometimes it is not possible for the wearer to recognize the condition of the shutter 14 by only looking through the shutter.

It will be appreciated that the operating circuitry 15 may have suitable detectors, operating software or firmware, and components, etc., to be able to determine which signals are to be directed to which indicators 20 to effect energization of such indicator(s) and the manner of energization, e.g., brightness, flashing, etc. The operating software or firmware may be written and the particular components of the operating circuitry 15 may be constructed by a person or persons having ordinary skill in the art based on the description herein. Moreover, as is described in the above-referenced and incorporated patents, various auto-darkening lenses and control systems are shown, and the present invention may be used, if desired, therewith.

While the auto-darkening lens 10 is worn, e.g., as part of a helmet 11, the indicators 20 generally may be observed by a wearer in the peripheral field of view of the wearer. As a wearer looks out through the shutter 14 toward work, such as an item being welded, brazed, glued, sanded, etc. in an industrial environment, or a dentist looks into the mouth of a patient, or a surgeon looks closely at an internal organ of a patient undergoing surgery, the indicators 20 generally may be seen in the peripheral field of view outside the ordinary direct field of view that the wearer intends to have in focus, e.g., while carrying out work in the focused field of view.

The indicators 20 may be the same so they provide the same color light output. The indicators 20 may be different. Differences may be such that the indicators are different sizes and/or shapes, produce different color light, different intensities of light, produce blinking (at respective frequencies) or no blinking, etc. The indicators may be aligned in a single horizontal row, e.g., parallel to the bottom edge 13b of the support 13, as is illustrated in FIG. 2; or the indicators may be at different locations. Each individual indicator may be one color light or a given indicator may be capable of providing different color light output, e.g., by using several closely positioned light emitting diodes that provide different color light or by using selective filters that can be turned on/off in response to energization, as a liquid crystal filter type device, for example. The indicators 20 may be operated to flash (e.g., to blink) or not, depending on information they are to convey to the wearer 12.

While the auto-darkening lens 10 is not in position in use on the head before the eyes of a wearer, the indicators 20 also may be seen by looking at them. In such case the indicators may be adequately far from the eyes of a person viewing them that the indicators may be seen in focus by the viewer's eyes. The indicators 20 may be used to provide information to a person who is adjusting the buttons and switches 18 indicating the settings made by such adjustments. Therefore, the indicators 20 may be used to provide valuable information both while in use before the eyes of the wearer and while not on the head of the wearer.

It will be appreciated that although the indicators 20 are illustrated and described as mounted on the support or housing 13, of the auto-darkening lens 10, the indicators may be positioned elsewhere. As an example, the indicators may be mounted on the welding helmet 11 itself.

Figures 3, 4:
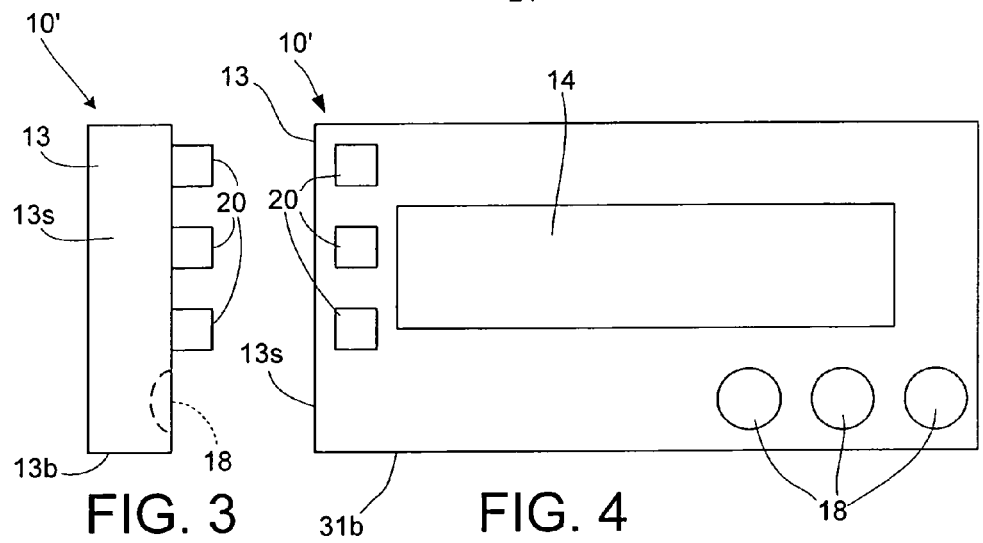
FIG. 3 is a side elevation view of an embodiment of auto-darkening lens with vertically oriented/spaced-apart indicators.
FIG. 4 is a back plan view of the auto-darkening lens of FIG. 3.

Turning to FIGS. 3 and 4, an embodiment of auto-darkening lens 10' in which the indicators 20 are in a vertically oriented/spaced apart relation is shown. The indicators 20 are aligned in a column at the left side edge 13s of the auto-darkening lens 10' adjacent the shutter 14 and are outside the usual field of view through the shutter while generally being in the peripheral field of view of the wearer to the left side of the head of the wearer. The auto-darkening lens 10' may be otherwise the same as the auto-darkening lens 10. Operation of the auto-darkening lens 10' may be the same as or similar to that described above for the auto-darkening lens 10.

Figures 5, 6:
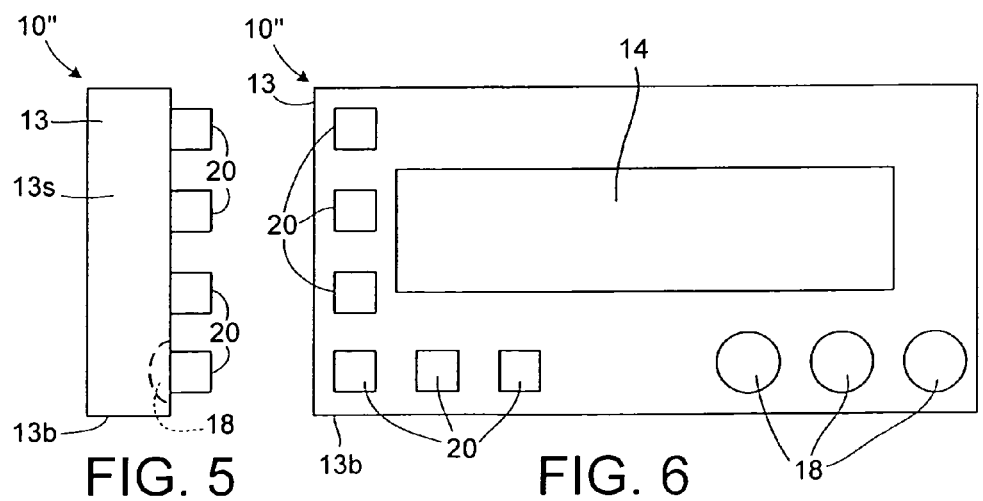
FIGS. 5 and 6 are, respectively, a side elevation view and a back plan view of an embodiment of auto-darkening lens with both horizontally/spaced-apart indicators and vertically/spaced-apart indicators.

If desired, the indicators 20 may be located both at a side edge and bottom edge of the shutter 14, e.g., on the support structure 13 side edge 13s and bottom edge 13b, as is illustrated schematically for an auto-darkening lens 10" in FIGS. 5 and 6.

Figure 7:
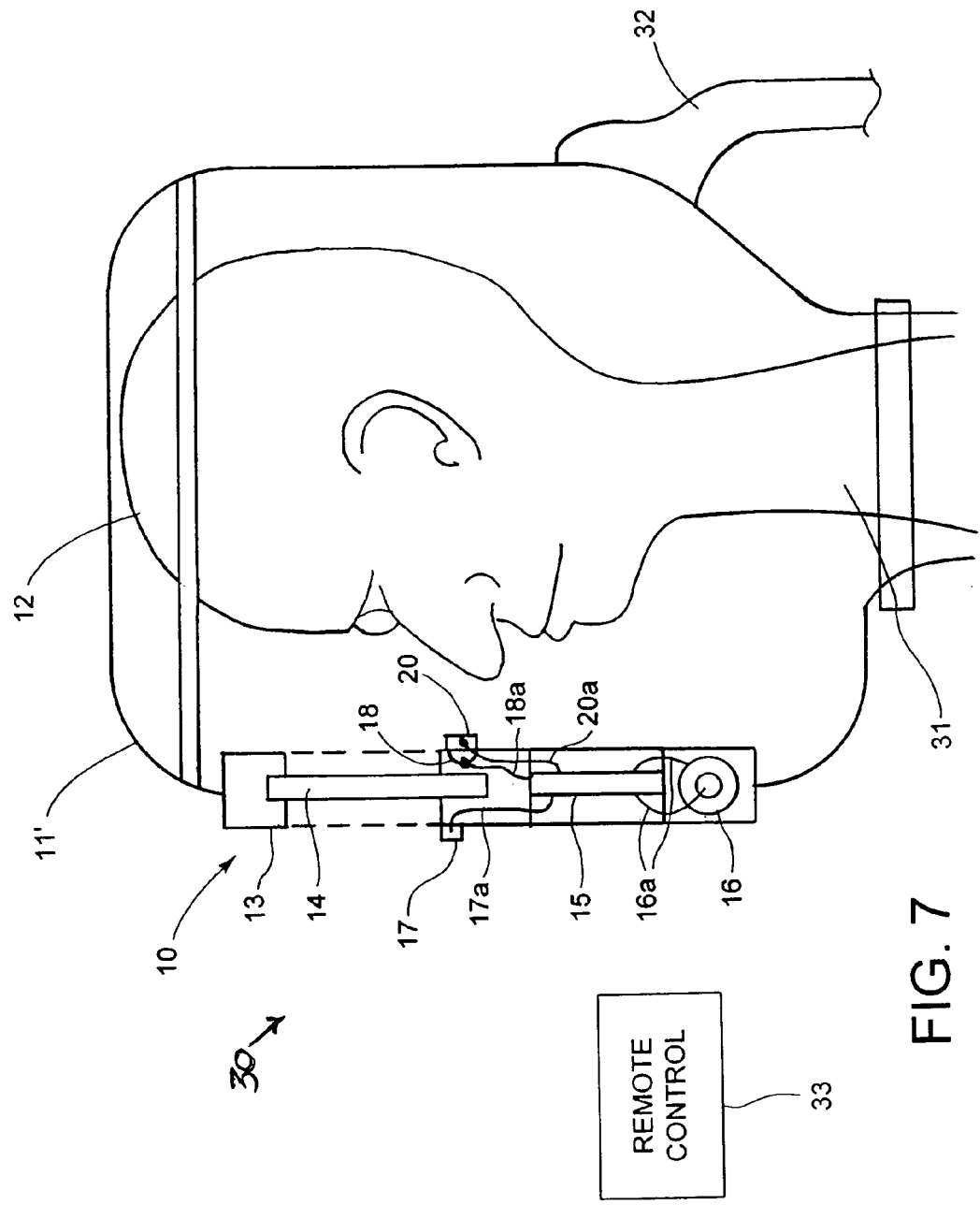

Referring to FIG. 7, a respirator 30 is illustrated schematically. The respirator 30 includes an auto-darkening lens 10 (or 10' or 10") mounted in a helmet structure 11' that fully encloses the head of a wearer and may be sealed to the neck of the wearer at 31 or may be part of an overall enclosure, such as a diving suit, space suit, or other suit typically used for entering hazardous environments. One or more tubes 32 provide air flow and, if desired, provide for exhausting the products of breathing with respect to the interior of the helmet structure 11'. The use and operation of the indicators 20 for the auto-darkening lens 10 in the respirator 30, etc., may be the same as is described above. If desired, a separate remote control schematically illustrated at 33 may be coupled by wire, radio signals, etc., to the operating circuitry 15 to allow the wearer of the respirator 30 and auto-darkening lens 10 to adjust the operative conditions, settings, etc., of the auto-darkening lens by manual or other operation of the wearer. Since it would be difficult and sometimes inadvisable for the wearer briefly to remove the auto-darkening lens 10 and respirator 30 to make such adjustments while wearing the respirator, the ability to make adjustments to settings of the auto-darkening lens 10 remotely may be advantageous. Furthermore, being able to discern the settings being made by remote control, perhaps by another person, as the user discerns the indicators 20 in the user's peripheral field of view, allows the user to confirm that proper settings are being made.

From the just described use of the indicators in a respirator or the like, it will be appreciated that the invention allows a wearer of the auto-darkening lens to discern meaningful operational, settings, etc., or other information even if the wearer is able to look directly at the indicators 20 but cannot obtain a focused view of the indicators, e.g., because the indicators are too close to the eyes.

Figure 8:
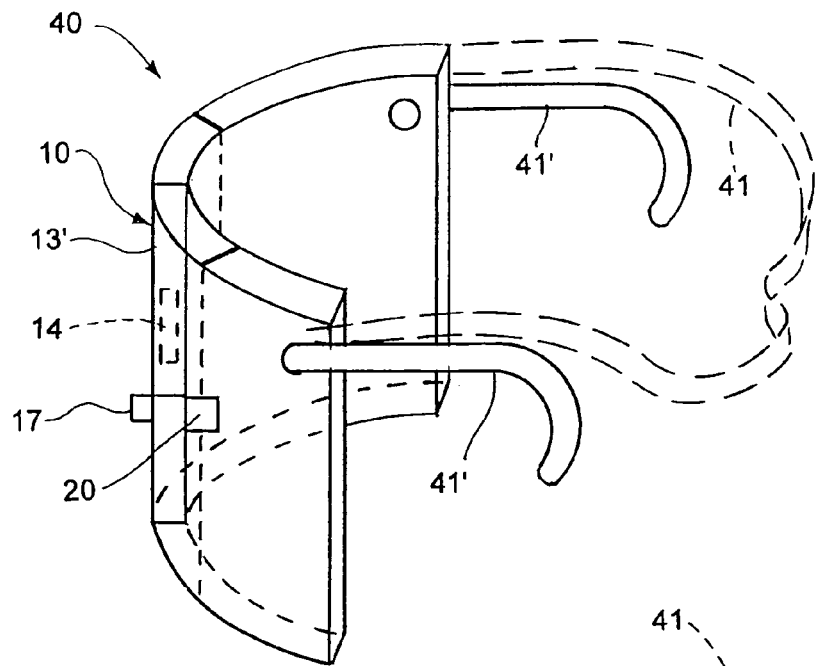
FIG. 8 is a schematic side elevation view of an auto-darkening lens in a dental shield face mask.

Briefly referring to FIG. 8, an auto-darkening lens 10 (or 10' or 10") is illustrated in a dental mask or face protector 40. The dental mask 40 may be clear plastic or other material or it may have a light blocking characteristic. With the auto-darkening lens 10, for example, mounted in the dental mask 40, e.g., to a support structure 13' thereof, and the dental mask 40 mounted on the head of a dentist, e.g., being held in place by a strap 41 or temple pieces 41' so as place the mask and the auto-darkening lens 10 in front of the face, the shutter 14 of the auto-darkening lens may be operated to protect the eyes of a dentist or dental technician from bright light and/or from light of a particular wavelength or wavelengths, e.g., ultraviolet used to cure a dental material, that might otherwise be harmful to the eyes, while the shutter still allows viewing therethrough absent such bright or possibly harmful light. The face protector 40 and the auto-darkening lens 10 also protect the face from particulates, fluids, etc. during dental procedures. Similarly, the dental mask 40 with the auto-darkening lens 10, for example, may be used by a surgeon conducting surgery, an industrial worker carrying out various tasks, and for other purposes, etc., to provide similar utility would be provided for a dentist.

Figure 9:
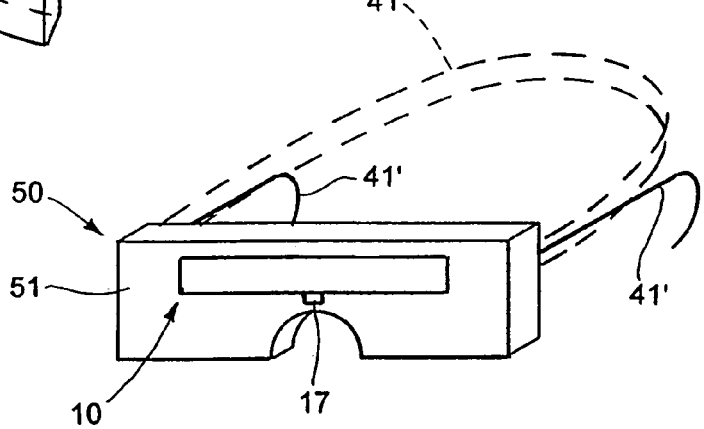
FIG. 9 is a schematic side elevation view of an auto-darkening lens in goggles.

Briefly referring to FIG. 9, the auto-darkening lens 10 (or 10' or 10") is shown in goggles 50. The goggles may be used for many different purposes, such as for protection in industrial environments, for racing automobiles or airplanes in an open cockpit, for observing experiments or other conditions in which bright light, even nuclear flash, may occur, etc. The goggles include a support structure 51, sometimes referred to as a frame, with appropriate components, as is schematically illustrated in FIG. 8, to allow the goggles to be worn on the head of a person. The auto-darkening lens may be mounted in such a support structure for use generally as was described above.

The goggles 50 may be in the form of eyeglasses that can be worn by a wearer. Such eyeglasses would include a support structure, such as a lens holder of an eyeglass frame, temple pieces to hold to the ears of a wearer, etc., as is schematically illustrated in FIG. 9. The eyeglasses 50 may use a lens 10 (or 10' or 10") that is a safety lens, which has a characteristic capable of meeting industrial standards of safety glasses for eye protection in an industrial plant.

Figure 10:
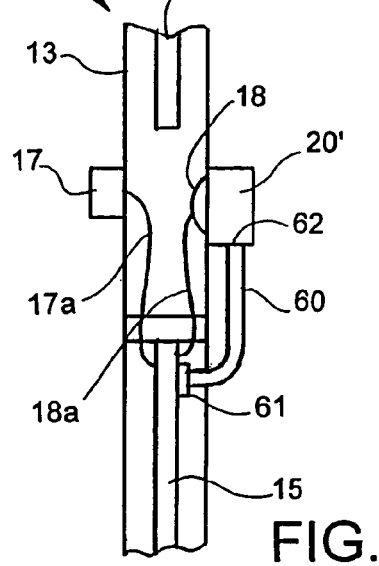
FIG. 10 is a schematic side elevation view of an auto-darkening lens with indicators that receive optical inputs.

Briefly referring to FIG. 10, an embodiment of auto-darkening lens 10''' that is similar to the other auto-darkening lenses 10, 10' and 10" is illustrated. The indicators 20' of the auto-darkening lens 10''' receive light from respective light conducting members, e.g., light pipes, fiber optic members, reflectors, etc., which are schematically illustrated at 60. A light input 61 to respective light conducting members 60 is provided from a source in the auto-darkening lens 10''', for example, from light emitting diodes or other devices on or associated with the operating circuitry 15, e.g., such light emitting devices may be mounted on a circuit board of the operating circuitry. The indicators 20' may be the light output end 62 of the respective light conducting members 60; or the light conducting members may provide light input to respective indicators to cause such indicators to provide a light output able to be seen by the wearer/user 12 (FIG. 1). The indicators 20' are positioned with respect to the auto-darkening lens 10''' in a manner the same or similar as the indicators 20 that are described above. The auto-darkening lens 10''' (and the other auto-darkening lenses described herein) may be used in the several devices described above, e.g., welding helmet, respirator, face shield, etc.

INDUSTRIAL APPLICATION

It will be appreciated that the aforementioned embodiments of the present invention may be used to provide indications of information concerning operating condition or other information in various environments in devices that use auto-darkening lenses and other devices in which viewing occurs in close proximity to one or more indicators.

I claim:

1. An indicator system for a head mountable apparatus, comprising
a number of indicators,
an input to provide selective inputs to the indicators to cause the indicators to provide output indications,
said indicators generally being in the peripheral field of view of only one eye of a wearer of such head mountable apparatus in ordinary use,
said indicators being located relative to each other, whereby the indications provided thereby may be comprehended based on at least one of relative location to each other and location in such head mountable apparatus.

2. The system of claim 1, wherein the indicators are so positioned in a head mountable apparatus as to be seen if such head mountable apparatus is off the head.

3. The system of claim 1, wherein the indicators are light emitting diodes.

4. The system of claim 1, wherein the indicators are located at one side of a center position of such head mountable apparatus as to be viewable primarily in the peripheral field of view of one eye of a wearer.

5. The system of claim 1, wherein the indicators comprise indicating devices to provide a light output and light conductors to conduct light from respective indicating devices to a location at the peripheral field of view of a wearer.

6. The system of claim 1, and further comprising in combination therewith a helmet.

7. The system of claim 6, wherein the helmet is a welding helmet.

8. The system of claim 6, wherein the helmet is part of a respirator.

9. The system of claim 6, wherein the helmet is a space helmet.

10. The system of claim 1, wherein the indicators provide light of different respecfrve colors.

11. A head mountable welding lens system including,
an indicator system comprising
a number of indicators,
an input to provide selective inputs to the indicators to cause the indicators to provide output indications,
said indicators generally being in the peripheral field of view of a wearer of such head mountable welding lens system in ordinary use.
said indicators being located relative to each other, whereby the indications provided thereby may be comprehended based on at least one of relative location to each other and location in such head mountable welding lens system, and
a variable transmission welding lens.

12. The welding lens system of claim 11, wherein the lens is an auto-darkening welding lens.

13. The welding lens system of claim 12, further comprising a sensor to sense welding and to provide a control to cause darkening of the welding lens.

14. The welding lens system of claim 11, further comprising an adjuster for adjusting at least one operative parameter of the welding lens, and wherein at least one indicator is operative to provide an indication of such adjusting of the operative parameter.

15. The welding lens system of claim 14, wherein said adjuster is a remote control.

16. The welding lens system of claim 14, wherein there are a number of adjusters, and each comprises a manual control device.

17. The welding lens system of claim 14, wherein the adjuster comprises a switch.

18. The welding lens system of claim 14, wherein the adjuster comprises a variable resistor.

19. The welding lens system of claim 11, wherein the welding lens includes a variable light transmission shutter and a support housing for the shutter, and wherein the indicators are mounted on the welding lens.

20. The welding lens system of claim 11, wherein said indicators that are in the peripheral field of view are only in the peripheral field of view of one eye of a wearer wearing the head mountable welding lens system to avoid confusion as to which one or more indicators is energized.

21. Eyeglasses including,
an indicator system, comprising
a number of indicators,
an input to provide selective inputs to the indicators to cause the indicators to provide output indications,
said indicators generally being in the peripheral field of view of a wearer of such eyeglasses in ordinary use,
said indicators being located relative to each other, whereby the indications provided thereby may be comprehended based on at least one of relative location to each other and location in such eyeglasses,
a frame and
a variable transmission viewing lens.

22. The eyeglasses of claim 21, wherein the lens is an auto-darkening lens.

23. The eyeglasses of claim 22, further comprising a sensor to sense light and to provide a control to cause darkening of the lens.

24. The Eyeglasses of claim 21, wherein said indicators that are in the peripheral field of view are only in the peripheral field of view of one eye of a wearer wearing the eyeglasses to avoid confusion as to which one or more indicators is energized.

25. Goggles including,
an indicator system comprising
a number of indicators,
an input to provide selective inputs to the indicators to cause the indicators to provide output indications,
said indicators generally being in the peripheral field of view of a wearer of such goggles in ordinary use,
said indicators being located relative to each other, whereby the indications provided thereby may be comprehended based on at least one of relative location to each other and location in such goggles,
a frame, and
a variable transmission viewing lens.

26. The goggles of claim 25, wherein the lens is an auto-darkening welding lens.

27. The goggles of claim 26, further comprising a sensor to sense light and to provide a control to cause darkening of the lens.

28. The goggles of claim 25, wherein said indicators that are in the peripheral field of view are only in the peripheral field of view of one eye of a wearer wearing the goggles to avoid confusion as to which one or more indicators is energized.

29. A protective apparatus for at least a portion of the face of a wearer, comprising
a protective shield positionable with respect to the face of a wearer,
a viewing area to permit viewing through the shield, and
a number of indicators to indicate information to a wearer,
the indicators being located at least one of relative to each other and to the shield to provide information to a wearer based on energization and location of such indicators,
wherein the protective shield includes an auto-darkening welding lens.

30. The apparatus of claim 29, wherein the indicators are mounted on the auto-darkening welding lens.

31. A protective apparatus for at least a portion of the face of a wearer, comprising
a protective shield positionable with respect to the face of a wearer,
a viewing area to permit viewing through the shield, and
a number of indicators to indicate information to a wearer,
at least some of the indicators being located in the peripheral field of view of only one eye of a wearer and being located at least one of relative to each other and to the shield to provide information to a wearer based on energization and location of such indicators.

32. The apparatus of claim 31, wherein the indicators are light emitting diodes.

33. The apparatus of claim 31, wherein the indicators emit light of different respective colors.

34. The apparatus of claim 31, further comprising light conductors for conducting light from the indicators to the peripheral field of view of a wearer.

35. The apparatus of claim 31, wherein the shield is a helmet.

36. The apparatus of claim 35, wherein the helmet is a welding helmet.

37. The apparatus of claim 35, wherein the helmet is part of a respirator.

38. The apparatus of claim 35, wherein the helmet is a space helmet.

39. A protective apparatus for at least a portion of the face of a wearer, comprising
   a protective shield positionable with respect to the face of a wearer,
   a viewing area to permit viewing through the shield, and
   means located for viewing only in the peripheral view of only one eye of a wearer for indicating information to a wearer by providing information to a wearer based on energization and location of such means for indicating relative to the field of view of a wearer.

40. A method of conveying information to a person wearing a device protecting at least part of the face, comprising
   selectively energizing one or more respective indicators positioned with respect to the peripheral field of view of only one eye of the person and to the device to convey information to the person based on the relative position of the respective energized one or more indicators to avoid confusion as to which one or more indicators is energized.

41. The method of claim 40, wherein the indicators are positioned relative to the field of view of a wearer as to be out of the direct field of view of the wearer with the device protecting at least part of the face in operative position to provide protection to a wearer.

42. The method of claim 40, further comprising using the device to provide shielding of at least part of the face.

43. The method of claim 40, wherein there are several indicators, and the information is based on relative position of at least one indicator to another indicator.

44. The method of claim 40, said selectively energizing comprising energizing respective indicators to carry information based on relative location of the one or more indicators to one or more other indicators.

45. A method of conveying information to a person wearing a device protecting at least part of the face, comprising
   selectively energizing one or more respective indicators positioned generally in the peripheral field of view of only one eye of the person.

* * * * *

UNITED STATES PATENT AND TRADEMARK OFFICE
CERTIFICATE OF CORRECTION

| | | |
|---|---|---|
| PATENT NO. | : 7,150,047 B2 | Page 1 of 1 |
| APPLICATION NO. | : 10/884047 | |
| DATED | : December 19, 2006 | |
| INVENTOR(S) | : Fergason | |

It is certified that error appears in the above-identified patent and that said Letters Patent is hereby corrected as shown below:

Column 11, line 16, replace "different respecfrve colors." with --different respective colors.--.

Signed and Sealed this

Twentieth Day of February, 2007

JON W. DUDAS
*Director of the United States Patent and Trademark Office*